(12) United States Patent
Maley

(10) Patent No.: US 6,921,529 B2
(45) Date of Patent: Jul. 26, 2005

(54) TREATMENT MODALITY AND METHOD FOR FUNGAL NAIL INFECTION

(76) Inventor: Joseph C. Maley, 18160 Cottonwood, #710, Sunriver, OR (US) 97707

( * ) Notice: Subject to any disclaimer, the term of this patent is extended or adjusted under 35 U.S.C. 154(b) by 0 days.

(21) Appl. No.: 10/207,936

(22) Filed: Jul. 29, 2002

(65) Prior Publication Data

US 2004/0019112 A1 Jan. 29, 2004

(51) Int. Cl.⁷ ............................. A61K 7/00; A61K 7/04; A61K 9/70; A01N 25/34
(52) U.S. Cl. ..................... 424/61; 424/401; 424/402; 424/443
(58) Field of Search ................................. 424/61, 401

(56) References Cited

U.S. PATENT DOCUMENTS

| | | |
|---|---|---|
| 4,721,724 A | 1/1988 | Stettendorf et al. |
| 5,151,271 A | 9/1992 | Otsuka et al. |
| 5,181,914 A | 1/1993 | Zook |
| 5,464,610 A | 11/1995 | Hayes, Jr. et al. |
| 5,683,713 A | 11/1997 | Blank et al. |
| 5,840,283 A | 11/1998 | Sorenson et al. |
| 5,972,317 A | 10/1999 | Sorenson et al. |
| 5,993,790 A | 11/1999 | Strauss |
| 6,042,845 A | 3/2000 | Sun et al. |
| 6,143,794 A * | 11/2000 | Chaudhuri .................. 514/655 |
| 6,159,977 A | 12/2000 | Reeves |
| 6,214,360 B1 | 4/2001 | Richter et al. |
| 6,231,840 B1 | 5/2001 | Buck |
| 6,264,927 B1 | 7/2001 | Monahan |

* cited by examiner

*Primary Examiner*—James M. Spear
*Assistant Examiner*—Sharon Howard
(74) *Attorney, Agent, or Firm*—Troutman Sanders LLP

(57) ABSTRACT

A method of treatment of onychomychosis wherein a hydrogel is supersaturated with an antimycotic agent and supported on a backing. The assembly is placed over an infected nail for an extended period of time. The antimycotic agent diffuses through the nail to the underlying infection.

18 Claims, 3 Drawing Sheets

TREATMENT MODALITY AND METHOD FOR FUNGAL NAIL INFECTION

This invention is related to the treatment of fungal nail infection, and in particular, to a novel anti-fungal agent and a method for its delivery.

BACKGROUND OF THE INVENTION

Onychomychosis, a fungal infection of the nail bed, is very common in the toes of humans and animals. The fungus becomes established and propagates under the nail, and typically deep at the root of the nail. The fungus causes breakdown and delamination of the nail, and is evidenced by a grainy appearance and discoloration of the nail. Untreated the infection can last for years, and can spread to adjacent toes.

No satisfactory treatment is known for fungal nail infection. Oral medications are available, but are expensive, require long treatment periods, involve possible toxicity, and are not reliable. The most common oral medication is Lamisil®. However, a regimen of Lamisil® costs $1,000 to $1,500, must be taken for about six months, and has an associated potential liver toxicity and other undesirable side effects. The success rate of Lamisil® is no better than about 80%, even at twice the normal length of treatment. For all these reasons physicians are reluctant to prescribe Lamisil® for what amounts to a minor (although objectionable) cosmetic condition.

Numerous topical treatments are available, including one requiring a prescription.

In most cases a yearlong treatment regimen requires application several times a day. Reliable clinical studies on the effectiveness of topical treatments are not available, but estimates of the success rates with topical treatments are less than 10%. This is thought to be true even when used as directed and for the full duration of one year, which is rarely done due to the long time involved and persistence required. They all suffer from low cure rates due to the fact that the antifungal agent applied rarely reaches all the fungus. No topical treatment currently available penetrates the nail well-enough to effectively deliver an anti-fungal agent to the sub-nail region where it is needed for effective treatment. Most of it evaporates off or is rubbed off long before it has a chance to penetrate. Addition of agents like DMSO or urea to improve penetration is only minimally effective.

The third method of treatment is surgical or chemical removal of the nail. Removal of the nail allows direct access to the site of the fungal infection. This is the most effective but least appealing to most people. There are also significant costs in addition to pain involved and the cure rate is about 80% at best.

A need therefore exists for a safe, effective and economical treatment of fungal nail infection.

DESCRIPTION OF PREFERRED EMBODIMENTS OF THE INVENTION

This invention is embodied in a composition and method for treating fungal nail infection in which a therapeutic agent such as a weak organic acid, preferably acetic acid, is dispersed in a polymeric matrix to form a supersaturated hydro-gel. The polymeric matrix is placed in contact with the affected nail, and the therapeutic agent is slowly released onto the surface of the nail in order to keep the nail wetted with the therapeutic agent. The makeup of the nail matrix is such that therapeutic agents in the form of weak acids will break down the matrix if given time. The continual wetting of the nail surface causes the therapeutic agent to break down the nail matrix, penetrate through the nail and reach and remedy the underlying fungal nail infection.

Turning now to FIGS. 1–7, onychomychosis is a fungal infection 10 that manifests below a finger or toe nail 12, and in the skin 14 underlying finger or toe nail 12. The infection is long lived and can spread to adjacent nails if not treated. The infection causes delamination of the nail and can cause the loss of the nail if not treated. Whether or not the entire nail is lost the infection is unsightly and generally undesirable. There are two main hurdles to effective treatment. First, the therapeutic agent must be delivered to the area beneath the nail. This requires either a systemic delivery or the penetration of the nail. Second, the treatment must continue for a sufficient period of time to be effective, normally six to twelve months for currently available treatments.

Figure 1:
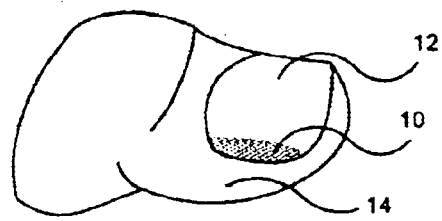
FIG. 1 illustrates a perspective view of a toe or a finger having a nail infected with a fungal infection.
Figure 2:
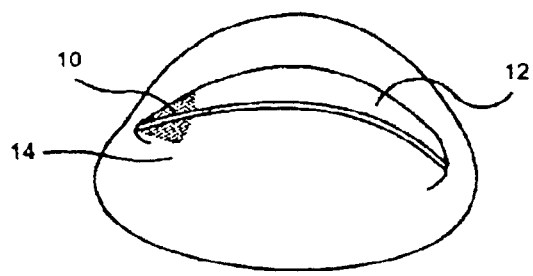
FIG. 2 illustrates a front view of a toe or a finger having a nail infected with a fungal infection.
Figure 3:
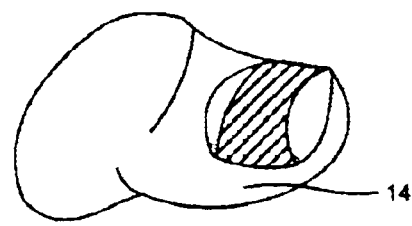
FIG. 3 illustrates a perspective view of a toe or a finger nail infected with a fungal infection.
Figure 4:
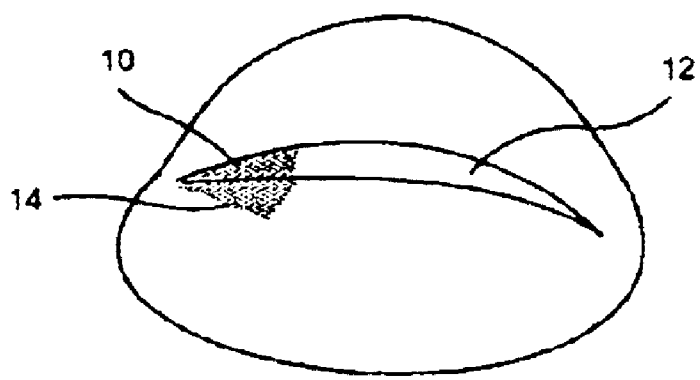
FIG. 4 illustrates a cross-sectional view of a toe or a finger having a nail infected with a fungal infection.
Figure 5:
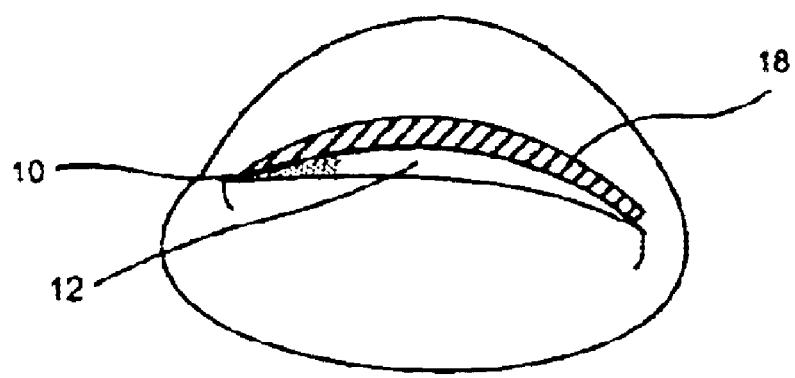
FIG. 5 illustrates a cross-sectional view of a nail fungus treatment patch in accordance with an embodiment of the present invention applied to a toe or a finger.
Figure 6:
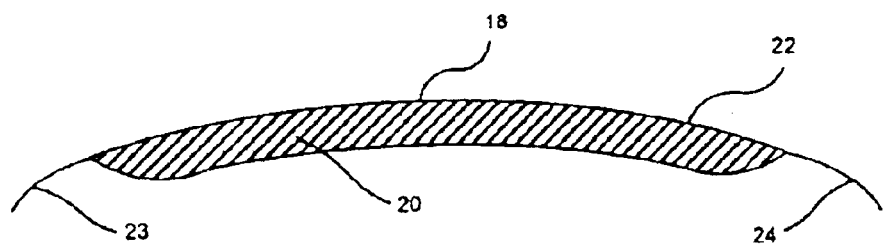
FIG. 6 illustrates a cross-sectional view of a fungal infection treatment patch in accordance with an embodiment of the present invention.
Figure 7:
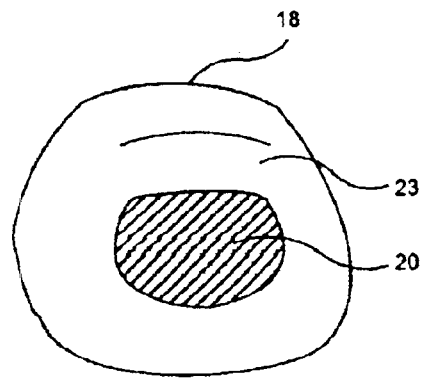
FIG. 7 illustrates a perspective view of a fungal infection treatment patch in accordance with an embodiment of the present invention.
Figure 8:
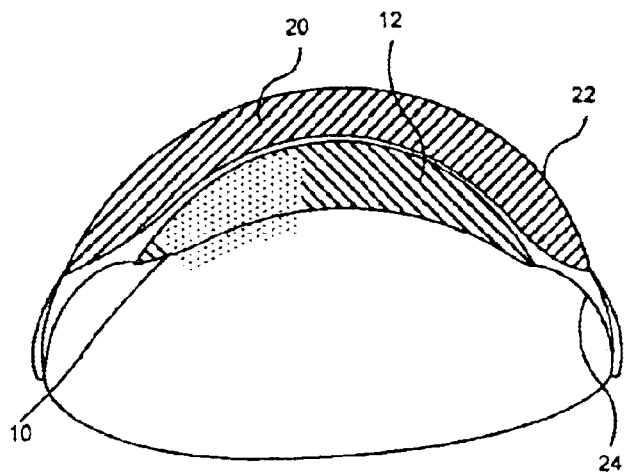
FIG. 8 illustrates a cross-sectional view of a nail fungus treatment patch in accordance with an embodiment of the present invention applied a toe or a finger nail.

This invention provides the first practical treatment for onychomychosis. Turning to FIGS. 5–7, one preferred embodiment the invention includes a patch 18 including a hydrogel 20 that has been supersaturated with a weak organic acid such as acetic acid. Jellylike hydro-gels, which are non-biodegradable polymers like polyacrylates, can absorb and retain many times their weight without dissolving. This supersaturated gel can be molded to a desired shape and covered with a membrane to form a "patch" that can be adhered to the surface of the toenail for prolonged contact between the supersaturated hydrogel and the nail. Once the supersaturated hydrogel is in contact with the nail, the therapeutic agent migrates from the hydrogel to the toenail surface, and will wet the surface until the hydrogel is depleted of therapeutic agent. The prolonged wetting of the toenail surface causes the therapeutic agent to diffuse into the toenail and eventually to the infection site beneath the toenail.

In one preferred embodiment the hydrogel is a polyacrylate, but any suitable hygroscopic hydrogel that is stable in acid solutions can be used in other embodiments. In FIGS. 6 and 7, Hydrogel 20 is supported on a backing 22 that is preferably shaped to roughly conform to the shape of nail 12. Backing 22 is preferably flexible to accommodate different nail sizes and shapes. The edges of backing 22 include adhesive portions 23 and 24 for securing the assembly in place on the toe.

Once in place on the toe, the hydrogel/acid solution is in contact with the surface of nail 12. The acid solution migrates slowly from the hydrogel and diffuses into nail 12. In the preferred embodiment sufficient hydrogel is provided to wet the toe surface for one day, and therefore a fresh bandage is applied daily. Applicant has determined that an amount of supersaturated hydrogel sufficient for one day can be provided in a patch that is relatively thin and therefore comfortable to wear for a number of days. Over a period of days, the acid solution diffuses through nail 12 (or the remaining intact portion thereof) and reaches the sight of the fungal infection. The infected portion of the nail, the underlying skin, and the fungus in each of those areas become saturated with the acid solution and the fungus is killed. Applicant has determined that effective treatment is normally achieved in about a week, although the treatment can be continued as long as necessary. In any event however, effective treatment will be achieved in significantly less than the months required by other treatments.

Reinfection is frequent with all treatments since the fungus often lives in dead skin (callous etc.) in other parts of the foot, and is not reached by any of the treatments including oral medications. Soaking the foot or hand in vinegar for one to two hours will penetrate the skin adequately to kill the fungus. For this reason, during the course of treatment the user might also elect to immerse the affected foot in a bath of acetic acid solution to avoid reinfection by fungus or fungal spores that have migrated from the affected area to surrounding areas.

The preferred embodiment described above includes a weak organic acid solution as the therapeutic agent and, in particular, citric acid. In other embodiments the therapeutic agent can include any other antimycotic agent with the ability to penetrate the nail over a course of several days. The antimycotic agent can be used alone or in conjunction with other active agents or carriers. Alternative therapeutic agents include but are not limited to iodine, DMSO, azole derivatives, undecylenic acid, tea tree oil, salicylic acid, urea, and any other recognized antimycotic agent. Other antimycotic agents might require alternate hydrogel solutions as could be readily determined by one of skill in the art of hydrogel solutions.

While the invention has been described with reference to the preferred embodiments above, those skilled in the art will appreciate that other combinations of therapeutic agent and hydrogel can be described, and other changes in detail and arrangement are possible without departing from the scope of the following claims.

What is claimed is:

1. A method of treating a nail infected with onychomycosis comprising,
    contacting an infected nail with a patch consisting of a cross-linked hydrogel wherein an organic acid solution is dispersed in the hydrogel.
2. The method according to claim 1 wherein the organic acid solution comprises citric acid.
3. The method according to claim 1, further comprising a supportive backing on a surface of the hydrogel.
4. The method according to claim 3 wherein the supportive backing is shaped to conform to an upper surface of an infected nail.
5. A method of treating a nail infected with onychomycosis, comprising,
    contacting an infected nail with a patch consisting of a cross-linked hydrogel wherein an organic acid solution is dispersed in the hydrogel, and diffusing the organic acid solution through at least a portion of the infected nail.
6. The method according to claim 5 wherein the organic acid solution comprises acetic acid.
7. The method according to claim 5 further comprising a supportive backing on a surface of the hydrogel.
8. The method according to claim 7 wherein the supportive backing is shaped to conform to an upper surface of an infected nail.
9. A treatment agent for an infected nail, consisting of:
    a supersaturated polymeric hydrogel;
    an organic acid dispersed in the hydrogel;
    a membrane to cover one surface of the hydrogel to form a patch; and
    an adhesive coupled one surface of the patch to attach the patch to the nail.
10. The treatment agent of claim 9 wherein the organic acid is acetic acid.
11. The treatment agent of claim 9 wherein the organic acid is citric acid.
12. The treatment agent of claim 9 wherein the hydrogel is a polyacrylate.
13. A treatment agent, consisting of:
    a supersaturated polymeric hydrogel;
    an antimycotic agent dispersed in the hydrogel;
    wherein the antimycotic agent is citric acid, acetic acid, iodine, DMSO, undecylenic acid, tea tree oil, salicylic acid, or urea;
    a membrane to cover one surface of the hydrogel to form a patch; and
    an adhesive coupled to one surface of the patch to attach the patch to the nail.
14. The treatment agent of claim 13 wherein the hydrogel is a polyacrylate.
15. The method of claim 1 wherein contacting further comprises adhering the cross-linked hydrogel to the infected nail.
16. The method of claim 5 wherein contacting further comprises adhering the cross-linked hydrogel to the infected nail.
17. The method according to claim 1 wherein the organic acid solution comprises acetic acid.
18. The method according to claim 5 wherein the organic acid solution comprises citric acid.

* * * * *